United States Patent [19]

Kamada et al.

[11] Patent Number: 5,776,067
[45] Date of Patent: Jul. 7, 1998

[54] METHOD OF DISPLAYING A BIPLANE IMAGE IN REAL TIME AND AN ULTRASONIC DIAGNOSING APPARATUS FOR DISPLAYING THE BIPLANE IN REAL TIME

[75] Inventors: Kazushi Kamada, Kashiwa; Shinichi Kondo, Asahikawa, both of Japan

[73] Assignee: Hitachi Medical Corporation, Tokyo, Japan

[21] Appl. No.: 785,254

[22] Filed: Jan. 17, 1997

[30] Foreign Application Priority Data

Jan. 19, 1996 [JP] Japan .................................. 8-024817

[51] Int. Cl.⁶ ...................................................... A61B 8/00
[52] U.S. Cl. ...................................... 600/443; 128/916
[58] Field of Search ........................ 128/660.07, 661.01, 128/916; 382/276, 289, 294; 600/407, 425, 443

[56] References Cited

U.S. PATENT DOCUMENTS

| | | | |
|---|---|---|---|
| 5,454,371 | 10/1995 | Fenster et al. | 128/916 X |
| 5,485,842 | 1/1996 | Quistgaard | 128/916 X |
| 5,608,849 | 3/1997 | King, Jr. | 128/660.07 X |
| 5,709,206 | 1/1998 | Teboul | 128/916 X |

*Primary Examiner*—Francis Jaworski
*Attorney, Agent, or Firm*—Reid & Priest LLP

[57] ABSTRACT

In a method of displaying a biplane image in real time in an ultrasonic diagnosing apparatus, ultrasonic waves are transmitted from a biplane probe to a portion of a sample to be diagnosed to scan two sectional planes that intersect orthogonally at an axis of intersection. Echo signals reflected from the sample portion are received by the probe. A tomographic image of each of the two orthogonal sectional planes is displayed on a display unit, each of the two displayed tomographic images being divided into two tomographic image planes along a line of intersection representing the axis of intersection of the two sectional planes. An image for inputting a visual field direction is also displayed on the display unit. Using an input device, a parameter indicating a chosen visual field direction is input to the image for inputting the visual field direction. Affine transformation parameters of the two displayed tomographic images are operated using the parameter of the chosen visual field direction. One of the two tomographic image planes of each of the two displayed tomographic images is selected, based on the parameter of the chosen visual field direction. The coordinates of the two displayed tomographic images are affine-transformed using the operated affine transformation parameters to deform the two displayed topographic images, the two deformed tomographic images being divided into two deformed tomographic image planes along the line of intersection. A three-dimensional image formed by coupling the planes of the two deformed tomographic images corresponding to the two tomographic image planes of the two displayed tomographic images which were previously selected, is displayed in real time.

16 Claims, 5 Drawing Sheets

VISUAL FIELD DIRECTION P
(ANGLE $\alpha_1$)

VISUAL FIELD DIRECTION P'
(ANGLE $\alpha_2$)

FIG.8

METHOD OF DISPLAYING A BIPLANE IMAGE IN REAL TIME AND AN ULTRASONIC DIAGNOSING APPARATUS FOR DISPLAYING THE BIPLANE IN REAL TIME

BACKGROUND OF THE INVENTION

The present invention relates to a method of displaying biplane image in real time in an ultrasonic diagnosing apparatus which displays a tomographic image obtained by transmitting ultrasonic waves to a portion to be diagnosed of a sample and receiving the ultrasonic waves in order to display tomographic images of two orthogonal sectional planes by scanning the two sectional planes that are intersecting at right angles on the same axis with respect to the portion to be diagnosed. More specifically, the invention relates to a method of displaying a biplane image in real time in an ultrasonic diagnosing apparatus that is capable of displaying tomographic images of the two orthogonal sectional planes as a three-dimensional image as viewed from any visual field direction.

DESCRIPTION OF THE RELATED ART

Figure 2:
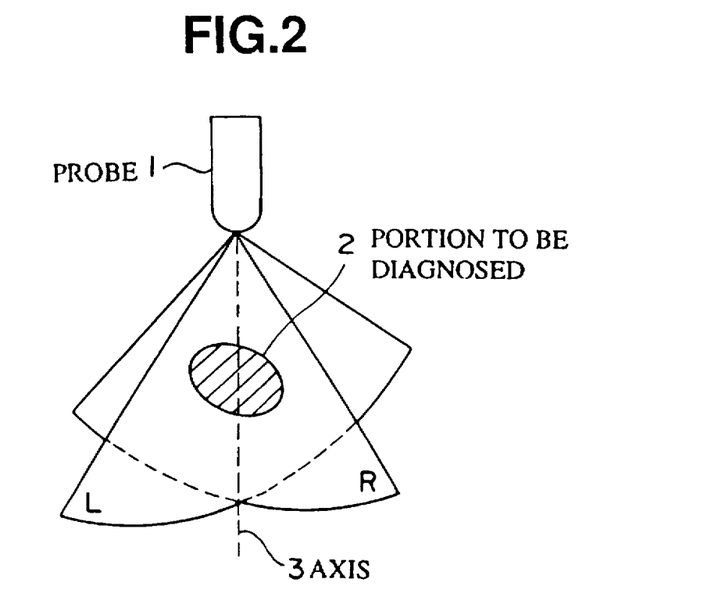
FIG. 2 is a perspective view illustrating a state where ultrasonic waves are transmitted from a probe to a portion to be diagnosed and are received to scan two sectional planes that are intersecting at right angles on the same axis according to the present invention and according to a conventional example.
Figure 8:
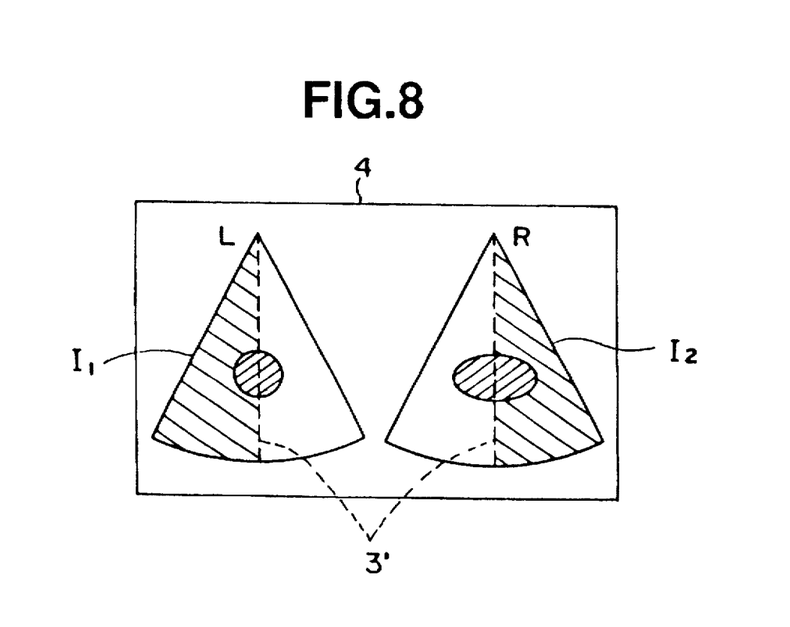
FIG. 8 is a diagram illustrating an image displayed by a conventional method of displaying biplane image in real time in an ultrasonic diagnosing apparatus.

According to a conventional ultrasonic diagnosing apparatus, ultrasonic waves are transmitted from a probe to a portion of a sample to be diagnosed and are received, the reflected echo signals that are received are subjected to the image-processing to constitute tomographic images of the portion to be diagnosed, and the tomographic images are displayed on a display unit. In a method of displaying a biplane image in real time in such an ultrasonic diagnosing apparatus, ultrasonic waves are transmitted from a biplane probe 1 to a portion 2 to be diagnosed as shown in FIG. 2 and are received to scan the two sectional planes L and R intersecting at right angles on the same axis 3. Then, as shown in FIG. 8, tomographic images $I_1$ and $I_2$ of the two orthogonal sectional planes L and R obtained by the scanning are displayed in real time being arranged on the same screen of a display unit 4. In this case, the tomographic image $I_1$ of one sectional plane L displayed on the screen of the display unit 4 is an image on a two-dimensional plane as viewed from the face direction of the other sectional plane R, and the tomographic image $I_2$ of the other sectional plane R is an image on a two-dimensional plane as viewed from the face direction of the above-mentioned one sectional plane L. In FIG. 8, reference numeral 3' denotes a line of intersection of the two orthogonal sectional planes L and R shown in FIG. 2.

In the above-mentioned conventional method of displaying a biplane image in real time, however, the data of the tomographic image are simply displayed, on the display unit 4, as independent tomographic images $I_1$ and $I_2$ of the two orthogonal sectional planes L and R which are two-dimensional plane images as shown in FIG. 8 despite the fact that the portion 2 to be diagnosed is scanned with an ultrasonic beam on the two orthogonal sectional planes L and R using a probe 1 as shown in FIG. 2 to collect three-dimensional tomographic data. Therefore, the three-dimensionally collected data of tomographic images were not at all utilized. In other words, a favorable image useful for diagnosis was not obtained. Therefore, a person who analyzes the image of diagnosis had to imagine a three-dimensional image from the combination of the two-dimensional tomographic images $I_1$ and $I_2$ (see hatched portions) to diagnose. This, however, required time and skill for the analysis often making it difficult to effect correct diagnosis.

SUMMARY OF THE INVENTION

The present invention was accomplished in order to cope with the above-mentioned problem, and its object is to provide a method of displaying a biplane image in real time in an ultrasonic diagnosing apparatus which is capable of displaying tomographic images of two orthogonal sectional planes as a three-dimensional image as viewed from any visual field direction.

In order to accomplish the above-mentioned object, with a method of displaying biplane image in real time in an ultrasonic diagnosing apparatus according to the present invention wherein ultrasonic waves are transmitted from a probe to a portion to be diagnosed of a sample and are received, the reflected echo signals that are received are subjected to image-processing to constitute a tomographic image of the portion to be diagnosed, and the tomographic image is displayed on a display unit, the ultrasonic waves are transmitted from said probe to the portion to be diagnosed and are received to scan two sectional planes that are intersecting at right angles on the same axis, tomographic images of the two orthogonal sectional planes obtained by the scanning are displayed, respectively, an image is displayed to input the visual field direction for the two orthogonal sectional planes, any visual field direction is input by using an input device for the image for inputting the visual field direction, affine transformation parameters are operated by using the input parameter of the visual field direction, the tomographic images of which planes among the planes of the two orthogonal sectional planes are to be selectively displayed are determined relying upon the parameter of the visual field direction, the coordinates of the tomographic images are affine-transformed by using said affine transformation parameters to deform the tomographic images, and the tomographic images of the deformed selected planes are displayed to display in real time the tomographic images of said two orthogonal sectional planes as a three-dimensional image as viewed from any visual field direction.

Thus, the tomographic images of the two orthogonal sectional planes can be displayed as a three-dimensional image as viewed from any visual field direction.

The tomographic images of which planes among the planes of the two orthogonal sectional planes are selected depending upon the parameter of the visual field direction may be the section of both the tomographic images of two planes in front of the line of intersection of the two orthogonal sectional planes with respect to the input visual field direction and the tomographic images of two planes at the back of the line of intersection.

This makes it possible to observe the portion of the sample to be diagnosed from various directions.

Furthermore, any visual field direction may be input, by using the input device, for the image for inputting the visual field directions by inputting two directions which are different in the adjacent planes among the planes of the two orthogonal sectional planes.

This makes it possible to observe the portion to be diagnosed of the sample from two different direction.

DETAILED DESCRIPTION OF THE PREFERRED EMBODIMENTS

Figure 1:
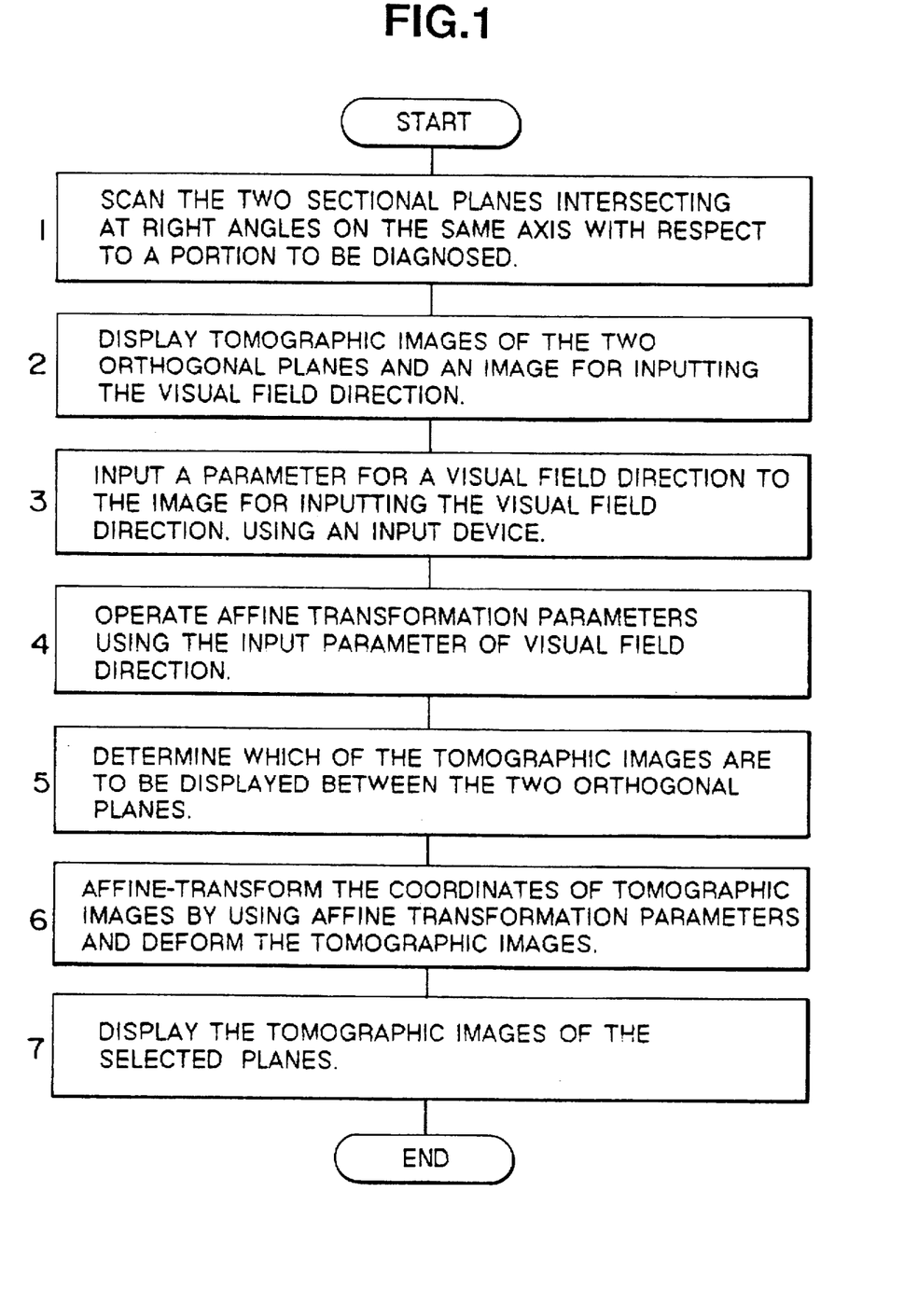
FIG. 1 is a flow chart illustrating the procedure of a method of displaying biplane image in real time in an ultrasonic diagnosing apparatus according to the present invention.

FIG. 1 is a flow chart illustrating the procedure of a method of displaying biplane image in real time in an ultrasonic diagnosing apparatus according to the present invention. In the ultrasonic diagnosing apparatus used for carrying out the method of displaying a biplane image in real time, ultrasonic waves are transmitted from a probe to a portion of a sample and to be diagnosed of a sample and are received, the reflected echo signals that are received are subjected to the image-processing to constitute a tomographic image of the portion to be diagnosed, and the tomographic image is displayed on a display unit. The ultrasonic diagnosing apparatus comprises, for example, a biplane probe, an ultrasonic wave transmitter/receiver, an A/D converter, an image-processing unit, an image memory unit, a D/A converter and a display unit, which are widely known.

The method of displaying biplane image in real time of the present invention carried out by using the above-mentioned ultrasonic diagnosing apparatus will now be described with reference to the flow chart of FIG. 1 and FIGS. 2 to 4. Referring, first, to FIG. 2, ultrasonic waves are transmitted from the probe 1 to a portion 2 of a sample to be diagnosed and are received to scan the two sectional planes L and R that are intersecting at right angles on the same axis 3 (step 1 in FIG. 1). Tomographic images of the two sectional planes L and R are thus obtained, respectively. Next, the tomographic images of the above two orthogonal sectional planes L and R are displayed, and an image for inputting the visual field direction is displayed, too (step 2). That is, in FIG. 3, the tomographic images 11 and 12 of the two orthogonal sectional planes L and R are displayed on the screen of a display unit 4, the tomographic image $I_1$ is divided into an a-plane and a b-plane and the tomographic image $I_2$ is divided into a c-plane and a d-plane with the line 3' of intersection of the two orthogonal sectional planes L, R as a boundary. There is at the same time displayed, on a part of the screen of the display unit 4, an image $I_3$ for inputting the visual field direction in a state where the axis 3 on which the two sectional planes L and R shown in FIG. 2 intersect at right angles is viewed from just the upper direction.

Figure 3:
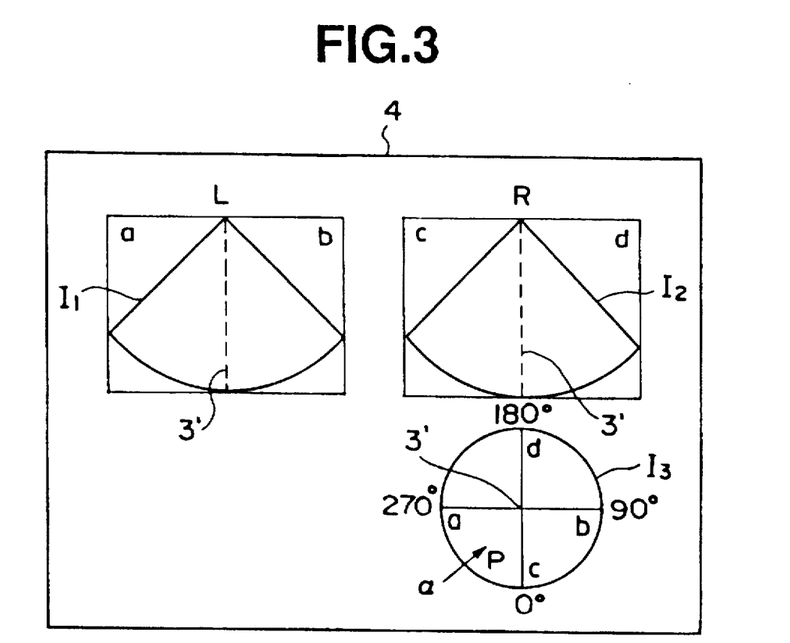
FIG. 3 is a diagram illustrating a state of displaying tomographic images of the two orthogonal sectional planes on a screen of a display unit and displaying an image for inputting the visual field direction in a state where the orthogonal axis is viewed from just the upper direction thereof according to the present invention.

Next, a given visual field direction is input using an input device for the image $I_3$ for inputting the visual field direction (step 3). That is, as shown in FIG. 3, an arrow P that represents the visual field direction is indicated on the image $I_3$ for inputting the visual field direction, the arrow P is turned about the line 3' of intersection by operating an input device such as encoder key or track ball provided on a keyboard and is set to a desired visual field direction. Thus, a parameter of a given visual field direction is input, for example, as an angle $\alpha$.

Then, affine transformation (coordinate transformation) parameters are operated by using the input parameter $\alpha$ of visual field direction (step 4). That is, the parameter $\alpha$ of the visual field direction is input to an affine transformation parameter operation means which consists of, for example, a CPU in the image-processing unit in order to operate affine transformation parameters $A_1$, $B_1$, $C_1$, $D_1$, $M_1$, $N_1$ for the tomographic image $I_1$ (a-plane and b-plane) and affine transformation parameters $A_2$, $B_2$, $C_2$, $D_2$, $M_2$, $N_2$ for the tomographic image $I_2$ (c-plane and d-plane) shown in FIG. 3 in a software manner as follows:

Angle $\alpha i$ of visual field for the tomographic image $I_1 = -\alpha$.

Angle $\alpha i$ of visual field for the tomographic image $I_2 = -\alpha + 90°$ If, $-90° \leq \alpha i < 90°$, then $A_1=1$ and $C_1=\tan \alpha i$. If, $-270° \leq \alpha i < -90°$, then $A_2=-1$ and $C_2=-\tan \alpha i$.

$B_1=B_2=0$ $D_1=D_2=1$ $M_1=M_2=0$ $N_1=N_2=0$.

It is then determined which of the halves of the tomographic images of sectional planes among L and R shown in FIG. 3 are to be displayed, that is, which of the tomographic images those of b-plane, c-plane and d-plane are to be displayed (step 5). The left image and the right image displayed as the three-dimensional image may be selected as follows depending upon the angle $\alpha$ of the visual field direction on the image $I_3$ for inputting the visual field direction.

| Value of $\alpha$ | left image | right image |
| --- | --- | --- |
| $\alpha = 0°$ | a | b |
| $0° < \alpha < 90°$ | c | b |
| $\alpha = 90°$ | c | d |
| $90° < \alpha < 180°$ | b | d |
| $\alpha = 180°$ | b | a |
| $180° < \alpha < 270°$ | d | a |
| $\alpha = 270°$ | d | c |
| $270° < \alpha < 360°$ | a | c |

Figure 4:
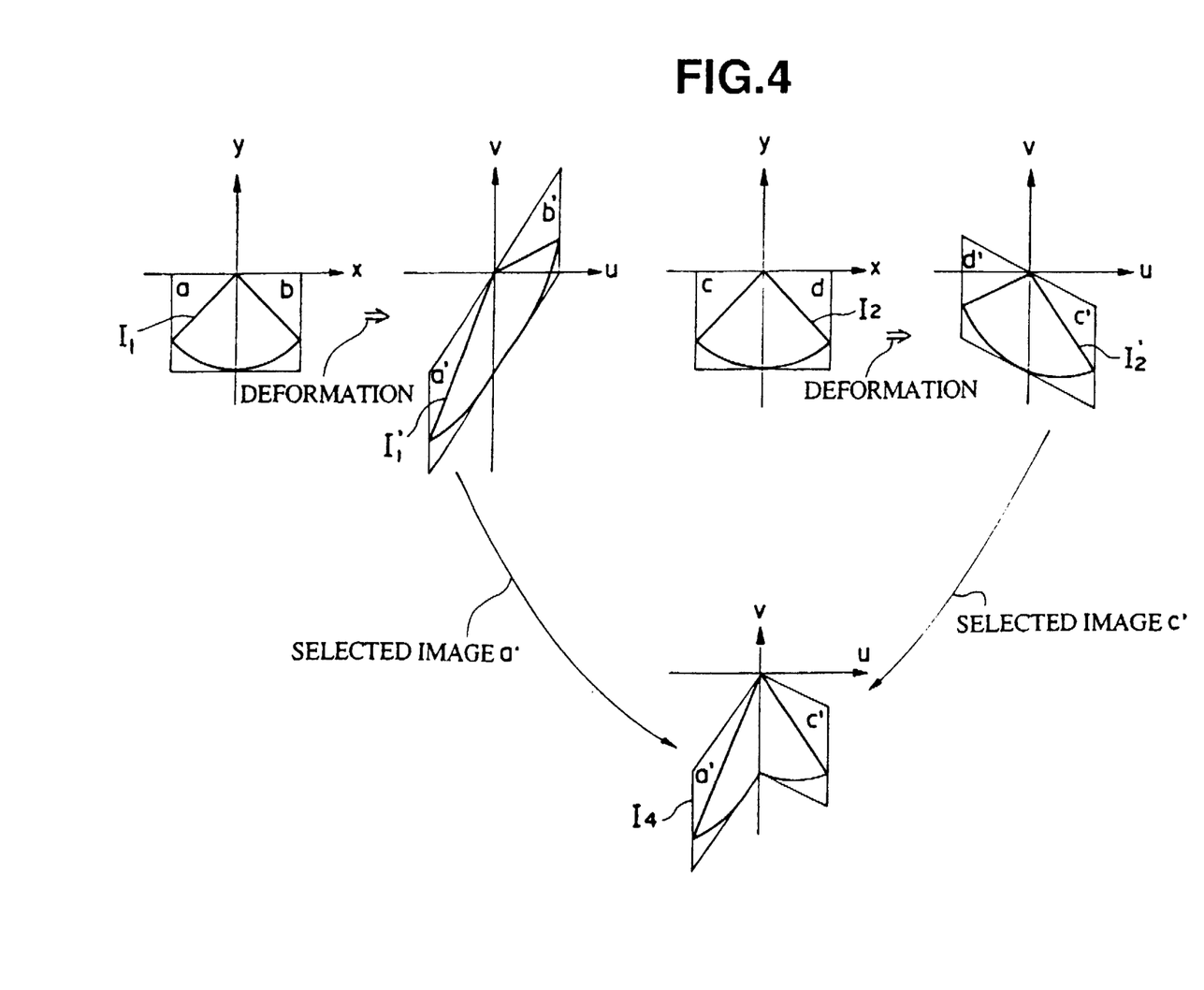
FIG. 4 is a diagram illustrating a state where coordinates of tomographic images of the two orthogonal sectional planes are affine-transformed to deform the tomographic images, and the selected images are displayed as a three-dimensional image.

Next, by using the affine transformation parameters $A_1$, $B_1$, $C_1$, $D_1$, $M_1$, $N_1$ and $A_2$, $B_2$, $C_2$, $D_2$, $M_2$, $N_2$, the coordinates of the tomographic images $I_1$ and $I_2$ are affine-transformed to deform the tomographic images $I_1$ and $I_2$ (step 6). That is, in FIG. 4, if the coordinates before transformation are denoted by (x,y) and the coordinates after transformation are denoted by (u,v), the affine transformation is expressed as $u = A_1 x + B_1 y + M_1$ $v = C_1 x + D_1 y + N_1$ \hfill (1)

for the tomographic image $I_1$, and is expressed as $$u = A_2x + B_2y + M_2$$
$$v = C_2x + D_2y + N_2 \quad (2)$$

for the tomographic image $I_2$.

This operation is executed by an affine transformation unit comprising a dedicated hardware or a digital signal processor in the image-processing unit. As a result, the tomographic image $I_1$ is deformed like a tomographic image $I_1'$ on the coordinates (u, v) and the tomographic image $I_2$ is deformed like a tomographic image $I_2'$ on the coordinates (u,v).

Then, the tomographic images of the planes selected at step 5 are displayed (step 7). That is, in step 5, the a-plane is selected as the left image and the c-plane is selected as the right image between the tomographic images $I_1$ and $I_2$. In FIG. 4, therefore, an a'-plane is taken out from the tomographic image $I_1'$ that has been deformed through the affine transformation, and a c'-plane is taken out from the tomographic image $I_2'$ that has been deformed through the affine transformation, and a tomographic image $I_4$ formed by coupling the two together on a v-axis is displayed. The tomographic image $I_4$ is displayed in real time as a three-dimensional image in a case that the two a- and c-planes adjacent to each other with the orthogonal axis 3 of the two orthogonal sectional planes L and R shown in FIG. 2 are simultaneously viewed from a visual field direction P (see FIG. 3).

The three-dimensional image displayed through the above-mentioned processing may so appear that a point of view changes up and down depending upon the value of the parameter a of the visual field direction. By correcting the affine transformation parameters $A_1$, $B_1$, $C_1$, $D_1$, $M_1$, $N_1$ and $A_2$, $B_2$, $C_2$, $D_2$, $M_2$, $N_2$ by the method of fluoroscopic projection, however, a proper point of view can be accomplished.

Described below are concrete examples of the affine transformation parameters and the affine transformation formula in a case that the parameter α of the visual field direction is 300°. First, the affine transformation parameters for the tomographic image $I_1$ (see FIG. 3) of the sectional plane L shown in FIG. 2 are, $$\alpha i = -300°, A_1 = 1, B_1 = 0$$
$$C_1 = \tan(-300°) = 1.73, D_1 = 1, M_1 = 0, N_1 = 0$$

By substituting these parameters for the above-mentioned formula (1), there is obtained the following affine transformation formula, $$u = x$$
$$v = 1.73x + y \quad (3)$$

Next, the affine transformation parameters for the tomographic image $I_2$ (see FIG. 3) of the sectional plane R shown in FIG. 2 are, $$\alpha i = -300° + 90° = -210°, A_2 = -1, B_2 = 0$$
$$C_2 = -\tan(-210°) = 0.57, D_2 = 1, M_2 = 0, N_2 = 0$$

By substituting these parameters for the above-mentioned formula (2), there is obtained the following affine transformation formula, $$u = -x$$
$$v = 0.57x + y \quad (4)$$

If the coordinates of the tomographic images $I_1$ and $I_2$ are affine-transformed in compliance with these affine transformation formulas (3) and (4), the tomographic images are deformed as shown in FIG. 4 mentioned above.

Figure 5:
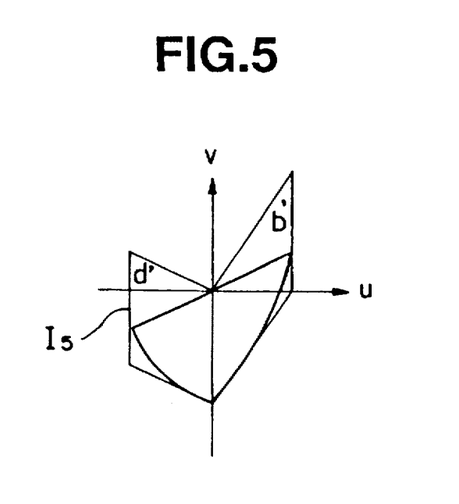
FIG. 5 is a diagram illustrating the method of displaying a second biplane image in real time according to another embodiment of the present invention.

FIG. 5 is a diagram illustrating a second affine-transformed and deformed tomographic image, which is displayed in parallel on the same screen on the display unit with the image shown in FIG. 4, in accordance with another embodiment of the method of displaying biplane image in real time according to the present invention. In this embodiment, the tomographic images of which planes among the planes of the two orthogonal sectional planes L, R to be selected depending upon the parameter α of the visual field direction, is the selection of both the tomographic images of two a- and c-planes in front of the line 3' of intersection of the two orthogonal sectional planes L and R and the tomographic images of two b- and d-planes at the back of the line 3' of intersection with respect to the input visual field direction P. In this case, the tomographic images of the two a- and c-planes in front of the line 3' of intersection are affine-transformed and deformed as shown in FIG. 4, and the a'- and c'-planes after being deformed are taken out and are displayed as a tomographic image $I_4$. The tomographic images of the two b- and d-planes at the back of the line 3' of intersection are similarly affine-transformed in FIG. 4 and are deformed, and the b'- and d'-planes after being deformed in the same manner are taken out and the two are coupled together on the v-axis so as to be displayed as a tomographic image $I_5$ as shown in FIG. 5. Here, if the tomographic image $I_4$ shown in FIG. 4 and the tomographic image $I_5$ shown in FIG. 5 are displayed in parallel on the same screen of the display unit, the portion 2 to be diagnosed shown in FIG. 2 can be observed from various directions.

Figure 6:
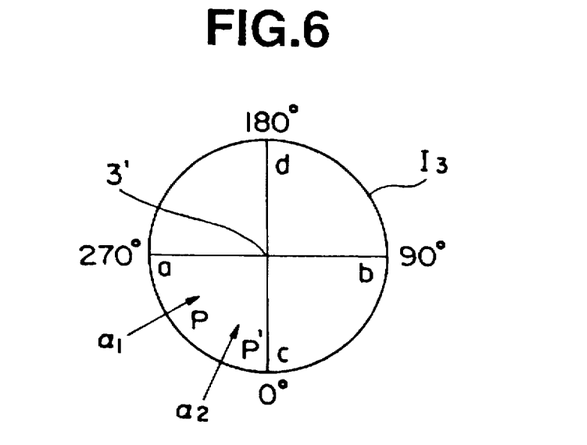
FIG. 6 is a diagram illustrating the method of displaying a biplane image in real time according to a further embodiment of the present invention.
Figure 7:
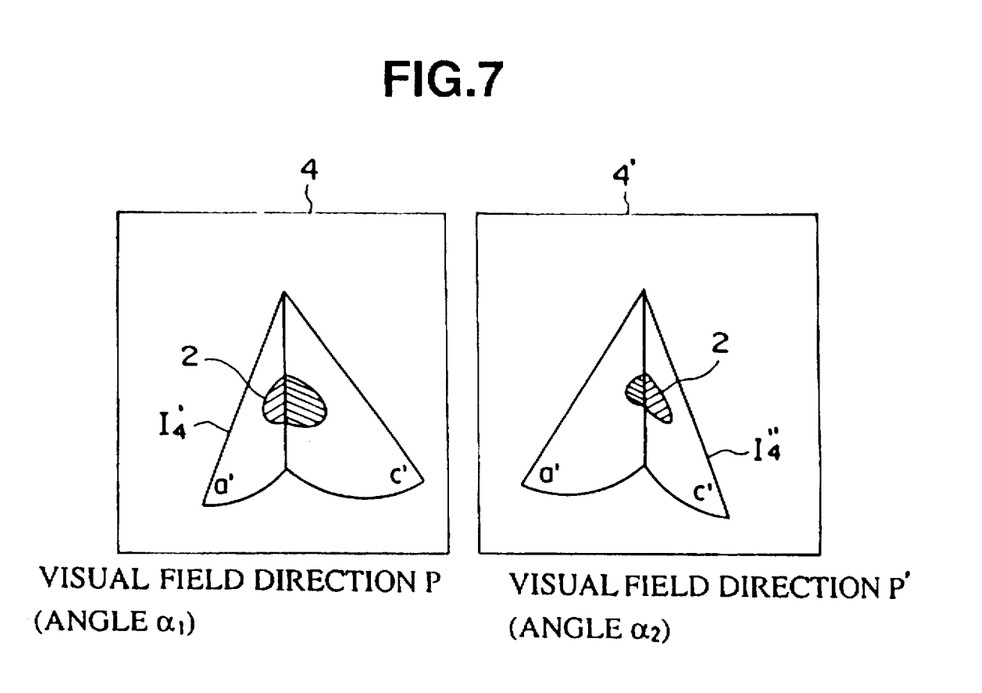
FIG. 7 is a diagram of a display example when a three-dimensional image is displayed according to the embodiment shown in FIG. 6.

FIG. 6 is a diagram illustrating a further embodiment of the method of displaying biplane image in real time according to the present invention. In this embodiment, any visual field direction P is input, by using the input device, for the image $I_3$ for inputting the visual field direction shown in FIG. 3 by inputting two directions which are different in the adjacent planes among the planes of the two orthogonal sectional planes L and R. That is, in FIG. 6, the two directions P and P' of visual fields are input between, for example, the a-plane and the c-plane among the planes of the two orthogonal sectional planes L, R with the line 3' of intersection as a center, the affine transformation parameters are operated by using angles α1 and α2 as parameters of visual field directions, and the coordinates of the tomographic images are affine-transformed by using the affine transformation parameters. As a result, there are simultaneously obtained a three-dimensional image I4' viewed from the visual field direction P and a three-dimensional image $I_4''$ viewed from the visual field direction P' as shown in FIG. 7. These images may be displayed on the screens of different display units 4 and 4', or may be displayed on the screen of the same display unit. In this case, the portion 2 to be diagnosed can be observed from the two different directions.

What is claimed is:

1. A method of displaying a biplane image in real time in an ultrasonic diagnosing apparatus, comprising the steps of:
   transmitting ultrasonic waves from a biplane probe to a portion of a sample to be diagnosed to scan simultaneously two sectional planes that intersect orthogonally at an axis of intersection;
   receiving with the probe echo signals reflected from the sample portion;
   displaying on a display unit a tomographic image of each of the two orthogonal sectional planes, each of the two displayed tomographic images being divided into two tomographic image planes along a line of intersection representing the axis of intersection of the two sectional planes;

also displaying on the display unit an image for inputting a visual field direction;

using an input device, inputting to the image for inputting the visual field direction a parameter indicating a chosen visual field direction;

operating affine transformation parameters of the two displayed tomographic images using the parameter of the chosen visual field direction;

selecting one of the two tomographic image planes of each of the two displayed tomographic images, based on the parameter of the chosen visual field direction;

affine transporting the coordinates of the two displayed tomographic images using the operated affine transformation parameters to deform the two displayed topographic images, the two deformed tomographic images being divided into two deformed tomographic image planes along the line of intersection; and displaying in real time a three-dimensional image formed by coupling the planes of the two deformed tomographic images corresponding to the two tomographic image planes of the two displayed tomographic images selected in said selecting step.

2. The method of claim 1, wherein said selecting step comprises selecting the plane of each of the two displayed tomographic images in front of the axis of intersection, with respect to the chosen input visual field direction, and selecting the plane of each of the two displayed tomographic images in back of the axis of intersection, with respect to the chosen input visual field direction.

3. The method of claim 1, wherein said selecting step comprises inputting two parameters indicating two different chosen visual field directions, the two different chosen visual field directions being located between adjacent planes of the two displayed tomographic images.

4. A method of displaying a biplane image in real time in an ultrasonic diagnosing apparatus, comprising the steps of:

transmitting ultrasonic waves from a biplane probe to a portion to be diagnosed and receiving the ultrasonic waves to scan simultaneously two sectional planes that intersect orthogonally at an axis of intersection;

displaying a tomographic image of the two orthogonal sectional planes obtained by the scanning, each of the two displayed tomographic images being divided into two tomographic image planes along a line of intersection representing the axis of intersection of the two sectional planes;

inputting information of at least one visual field direction for viewing the two orthogonal sectional planes;

using the input information of the visual field direction, selecting which of the tomographic images are to be deformed;

deforming at least the coordinates of the selected tomographic images using the input information of the visual field direction; and displaying the deformed tomographic images.

5. The method of claim 4, wherein said step of inputting information comprises inputting information of at least two visual field directions for viewing the two orthogonal sectional planes, wherein the at least two visual field directions are between two tomographic image planes of the two displayed tomographic images which are adjacent.

6. A method of displaying a biplane image in real time in an ultrasonic diagnosing apparatus, comprising the steps of:

transmitting ultrasonic waves from a biplane probe to a portion to be diagnosed and receiving the ultrasonic waves to scan simultaneously two sectional planes that intersect orthogonally at an axis of intersection;

displaying a tomographic image of the two orthogonal sectional planes obtained by the scanning, each of the two displayed tomographic images being divided into two tomographic image planes along a line of intersection representing the axis of intersection of the two sectional planes;

inputting information of at least one visual field direction for viewing the two orthogonal sectional planes;

deforming the coordinates of the two tomographic image planes of each of the tomographic images using the information of the at least one visual field direction to deform the tomographic image planes;

selecting one of the two tomographic image planes of each of the tomographic images, using the information of the at least one visual field direction; and displaying the deformed tomographic image planes corresponding to the selected tomographic image planes.

7. The method of claim 6, wherein said step of inputting information comprises inputting information of at least two visual field directions for viewing the two orthogonal sectional planes, wherein the at least two visual field directions are between two tomographic image planes of the two displayed tomographic images which are adjacent.

8. A method of displaying a biplane image in real time in an ultrasonic diagnosing apparatus, comprising the steps of:

transmitting ultrasonic waves from a biplane probe to a portion to be diagnosed and receiving the ultrasonic waves to scan simultaneously two sectional planes that intersect orthogonally at an axis of intersection;

inputting information of at least one visual field direction for viewing the two orthogonal sectional planes;

designating any region divided by said two orthogonal sectional planes;

deforming tomographic images of at least the designated region based on the information of the at least one visual field direction; and displaying the deformed tomographic images of the designated region.

9. The method of claim 8, wherein said step of inputting information comprises inputting information of at least two visual field directions for viewing the two orthogonal sectional planes.

10. The method of claim 9, wherein said step of deforming tomographic images comprises deforming tomographic images of at least the designated region based on the information of one of the at least two visual field directions; and wherein said displaying step comprises displaying the deformed tomographic images of the designated region, at least one of the tomographic images of the designated region being displayed by switching from one to another of the information of one of the at least two visual field directions in said deforming step.

11. A method of displaying a biplane image in real time in an ultrasonic diagnosing apparatus, comprising the steps of:

transmitting ultrasonic waves from a biplane probe to a portion to be diagnosed and receiving the ultrasonic waves to scan simultaneously two sectional planes that intersect orthogonally at an axis of intersection;

inputting information of at least one visual field direction for viewing the two orthogonal sectional planes;

deforming tomographic images of the two orthogonal sectional planes in any region divided by the two orthogonal sectional planes based on the information of the at least one visual field direction;

designating any region divided by the two orthogonal sectional planes; and displaying the deformed tomographic images in the designated region.

12. The method of claim 11, wherein said step of inputting information comprises inputting information of at least two visual field directions for viewing the two orthogonal sectional planes.

13. The method of claim 11, wherein said step of deforming tomographic images comprises deforming tomographic images of the two orthogonal sectional planes in any region divided by the two orthogonal sectional planes based on the information of one of the at least two visual field directions; and wherein said displaying step comprises displaying the deformed tomographic images in the designated region, at least one of the tomographic images in the designated region being displayed by switching from one to another of the information of one of the at least two visual field directions in said deforming step.

14. An ultrasonic diagnosing apparatus comprising:

biplane probe means for transmitting ultrasonic waves to a portion of a sample to be diagnosed and receiving the ultrasonic waves to scan simultaneously two sectional planes that intersect orthogonally at an axis of intersection; and tomographic image display means for displaying tomographic images of the portion as viewed from a view point placed anywhere in any region formed by the two orthogonal sectional planes.

15. The apparatus of claim 14, further comprising pseudo-three-dimensional image display means for displaying tomographic images of the sample as viewed from at least two view points to create a pseudo-three-dimensional image.

16. The apparatus of claim 14, wherein said tomographic image display means functions to display tomographic images of the portion as viewed from at least two view points placed anywhere in any region formed by the two orthogonal sectional planes; and wherein said apparatus further comprises pseudo-three-dimensional image display means for displaying a pseudo-three-dimensional image created by switching from one to another of the at least two view points.

* * * * *